United States Patent
Ruffert et al.

(10) Patent No.: US 8,277,615 B2
(45) Date of Patent: Oct. 2, 2012

(54) METHOD FOR THE DISTILLATIVE PURIFICATION OF SLOW-EVAPORATING FLUIDS

(75) Inventors: Gerhard Ruffert, Leverkusen (DE); Oliver Pfohl, Leverkusen (DE); Marcus Grün, Shanghai (CN)

(73) Assignee: Bayer Technology Services GmbH, Leverkusen (DE)

( * ) Notice: Subject to any disclaimer, the term of this patent is extended or adjusted under 35 U.S.C. 154(b) by 1177 days.

(21) Appl. No.: 11/909,343

(22) PCT Filed: Mar. 21, 2006

(86) PCT No.: PCT/EP2006/002553
§ 371 (c)(1),
(2), (4) Date: May 7, 2008

(87) PCT Pub. No.: WO2006/100023
PCT Pub. Date: Sep. 28, 2006

(65) Prior Publication Data
US 2008/0283383 A1    Nov. 20, 2008

(30) Foreign Application Priority Data
Mar. 22, 2005    (DE) .......... 10 2005 013 030

(51) Int. Cl.
*B01D 3/00* (2006.01)
*B01D 3/34* (2006.01)
(52) U.S. Cl. .......... 203/39; 203/50
(58) Field of Classification Search .......... 203/29, 203/41, 50, 99, 51
See application file for complete search history.

(56) References Cited

U.S. PATENT DOCUMENTS

| | | | | |
|---|---|---|---|---|
| 2,080,064 | A * | 5/1937 | Roelfsema | 568/913 |
| 2,357,028 | A * | 8/1944 | Shiras et al. | 203/58 |
| 3,689,375 | A | 9/1972 | Furukawa et al. | |
| 4,726,894 | A | 2/1988 | Ryskamp et al. | |
| 4,874,473 | A * | 10/1989 | Arlt et al. | 203/1 |
| 5,811,573 | A * | 9/1998 | Nishihira et al. | 560/146 |
| 6,616,831 | B1 * | 9/2003 | Gentry et al. | 208/313 |
| 8,002,953 | B2 * | 8/2011 | Lee et al. | 203/19 |
| 2004/0133058 | A1 * | 7/2004 | Arlt et al. | 585/833 |

FOREIGN PATENT DOCUMENTS

| | | |
|---|---|---|
| DE | 3613975 A1 | 10/1987 |
| DE | 10336555 * | 2/2005 |

OTHER PUBLICATIONS

J.P. Garcia Villaluenga, A. Tabe Mohammadi, "A review on the separation of benzene/cyclohexane mixtures by pervaporation processes", Journal of Membrane Science, vol. 169 pp. 159-174, Elsevier (c) 2000.*

(Continued)

*Primary Examiner* — Robert A Hopkins
*Assistant Examiner* — Patrick McCarty
(74) *Attorney, Agent, or Firm* — Norris McLaughlin & Marcus PA (57) ABSTRACT

The present invention relates to a method for removing volatile compounds from sparingly volatile fluids by means of rectification using an auxiliary and also to separation methods and chemical reactions in which sparingly volatile fluids are used, the purification of which is effected by means of rectification and using an auxiliary.

1 Claim, 1 Drawing Sheet

Extractive distillation                Purification

OTHER PUBLICATIONS

Seiler, M., Kohler, D., Arlt, W., "Hyperbranched polymers: new selective solvents for extractive distillation and solvent extraction", Separation and Purification Technology, vol. 29 pp. 245-263, Elsevier (c) 2002.*

Kragyl, U., Eckstein, M., Kaftzik, N., "Enzyme catalysis in ionic liquids", Current Opinion in Biotechnology, vol. 13 issue 6 pp. 565-571, Elsevier (c) 2002.*

Seiler, M., Kohler, D., Arlt, W. "Hyperbranched polymers: new selective solvents for extractive distillation and solvent extraction", Seperation and Purification Technology, vol. 30 pp. 179-197, (c) 2003 Elsevier.*

Seiler, M., Jork, C., Kavarnou, A., Arlt, W.,Hirsch, R., "Separation of Azeotropic Mixtures Using Hyperbranched Polymers or Ionic Liquids", AlChE Journal, vol. 50 No. 10, (c) 2004 American Institute of Chemical Enigneers.*

Theodor Grewer: "Trennung von Chlorwasserstoff un Wasser durch extraktive Destillation mit Schwefelsaure" Chemie Ingenieur Technik—CIT, col. 43, No. 11, Jun. 1971, pp. 655-658.

Garcia Villaluenga J P et al: "A review on the separation of benzene/cyclohexane mixtures by pervaporation processes" Journal of Membrane Science, Elsevier Science, vol. 169, No. 2, May 2000, pp. 159-174.

Patent Abstracts of Japan, vol. 1997, No. 10, Oct. 31, 1997.

Albrecht Salzer: Chemical & Engineering News, Apr. 29, 2002, p. 4.

Andreas Heintz: "Thermodynamic Properties of Mixtures . . . " J. Chem. Eng. Data, 2001, vol. 46, pp. 1526-1529.

Thomas Welton: "Room-Temperature Ionic Liquids. Solvents for Synthesis and Catalysis" Chemistry Reviews, 1999, vol. 99, No. 8, pp. 2071-2083.

Chrisitan Reichardt: "Empirical Parameters of Solvent Polarity from Spectroscopic Measurements" Solvents and Solvent Effects in Organic Chemistry (Third Edition), p. 241, 2003.

Henri Renon: "Local Compositions in Thermodynamic Excess Functions for Liquid Mixtures", AlChE Journal, vol. 14, No. 1, pp. 135-144.

Anders Hult: "Hyperbranched Polymers", Advances in Polymer Science, 1999, vol. 143, pp. 1-34.

Young H. Kim: "Hyperbranched Polymers 10 Years After" Journal of Polymer Science: Part A; Polymer Chemistry, vol. 36, pp. 1685-1698, 1998.

Johann Stichlmair: "Distillation—Principles and Practice", Journal of Chemical Technology & Biotechnology, 1999, vol. 74, pp. 240-244.

Peter Wasserscheid: "Ionische Flussigkeiten", Angewandte Chemie, 1999.

Theodor Grewer: "Trennung von Chlorwasserstoff und Wasser durch extraktive Destillation mit Schwefelsäure" Chemie Ingenieur Technik—CIT, vol. 43, No. 11, Jun. 1971, pp. 655-658, XP002385737.

Garcia Villaluenga J P. et al: "A review on the separation of benzene/cyclohexane mixtures by pervaporation processes" Journal of Membrane Science, Elsevier Science, Amsterdam, NL, vol. 169, No. 2, May 2000, pp. 159-174, XP004191967, ISSN: 0376-7388, p. 164; figures 4,5.

Patent Abstracts of Japan, vol. 1997, No. 10, Oct. 31, 1997 & JP 09 165348 A (Mitsubishi Chem Corp), Jun. 24, 1997.

* cited by examiner

Fig. 1 (Prior Art)

Extractive distillation          Purification

Fig. 2

Extractive distillation          Purification

METHOD FOR THE DISTILLATIVE PURIFICATION OF SLOW-EVAPORATING FLUIDS

This application is a 371 application of PCT/EP2006/002553 filed Mar. 21, 2006, which claims priority to the German application DE 10 2005 013 030.5 filed Mar. 22, 2005.

FIELD OF THE INVENTION

The present invention relates to a method for removing volatile compounds from sparingly volatile fluids by means of rectification using an auxiliary. The purpose of the auxiliary is to be able to obtain an arbitrarily low residual content of the volatile compounds to be removed in the bottom of the column under industrially expedient conditions with regard to pressure and temperature in the evaporator of the column.

BACKGROUND OF THE INVENTION

Sparingly volatile fluids, such as, for example, ionic liquids or liquid polymers, are becoming more and more popular in process engineering because their low vapor pressure has various advantages. They are readily used as process solvents since the proportion of the organic impurities in the atmosphere (VOC) is reduced thereby; in addition, they are used as auxiliaries in the separation of substances.

For the industrial separation of mixtures of substances, multistage distillation under reflux, in short rectification, is frequently used. Key elements of rectification column are the evaporator in the bottom, by means of which an ascending vapor stream is produced, and the condenser at the top, by means of which a descending liquid stream is produced. Ascending vapor stream and descending liquid stream are brought into intensive contact with one another on internals. By means of the countercurrent thus produced, it is possible to adjust the composition of the streams at the top and bottom of the column within wide ranges with the aid of the column parameters height and reflux ratio when rectification section and stripping section are used. A large number of mixtures which cannot easily be separated by conventional rectification but preferably by extractive rectification [Stichlmair, S. and Fair, J., Distillation, ISBN 0-471-25241-7, Page 241 et seq., or Gmehling and Brehm, "Grundoperationen—Lehrbuch der Technischen Chemie, Band 2" [Basic operations—Textbook of Industrial Chemistry, volume 2], Thieme Verlag, 1996] occur in industry. This state of affairs is due to the similar boiling behavior of the components of the mixture, i.e. to their property of being distributed between the vapor phase and liquid phase in virtually identical or identical molar concentration ratio at a defined pressure and a defined temperature. A procedure frequently practiced in industry for separating close-boiling—the separation factor $\alpha_{ij}$ (ratio of the partition coefficients of the components i and j) of less than 1.2 is usually understood by this—or azeotropic systems is the addition of a selective additive, the so-called entrainer, in an extractive rectification. By selective interactions with one or more of the components of the mixture, a suitable additive influences the separation factor in the rectification so that the separation of the close-boiling or azeotropically boiling components of the mixture is permitted. The advantage of using a sparingly volatile liquid as an entrainer is as described in DE 10136614 and EP 1372807 for ionic liquids or in DE 10160518 for hyperbranched polymers—that the low vapor pressure of the entrainer prevents or minimizes contamination of the top component by the entrainer.

A second method which is frequently used in industry for separating azeotropic or close-boiling mixtures is liquid-liquid extraction [Sattler, K., Thermische Trennverfahren [Thermal separation methods], ISBN 3-527-28636-5, Chapter 6]. In this method, the liquid feed to be separated is passed countercurrently to a liquid, selective absorbing phase, the solvent in selected extraction columns. The intensive mass transfer between feed and absorbing phase results in the absorbing phase becoming enriched with one or more components of the feed and leaving the extraction column as an extract stream. The feed stream which is depleted in the components which have passed over into the extract stream is taken off as a raffinate stream from the extraction column. Both extract stream and raffinate stream can then be fed to separate rectification columns in which the respective stream can be separated into the individual components. Sparingly volatile liquids may expediently also be used as solvent as described in DE 10160518 for hyperbranched polymers or in "Ionic Liquids in Synthesis" (P. Wasserscheid and T. Welton, Wiley-VCH, ISBN 3-527-30515-7) for ionic liquids. Instead of extraction columns, other one-stage or multistage apparatuses, e.g. so-called mixer-settlers, are also used for liquid-liquid extraction.

Membrane separation methods constitute a third generic type of separation methods encountered in industry. The membrane separation methods utilize the fact that some components are transported through a membrane from a fluid feed stream more rapidly than other components. In this way, a permeate stream is obtained behind the membrane and, analogously to the liquid-liquid extraction, a retentate stream depleted in at least one component. A solvent can be used behind the membrane in order to improve the separation effect (so-called pertraction—permeation and extraction) or in order to be able to use an electric field, such as, for example, membrane electrophoresis or electrofiltration/electrodialysis, where an electric field is applied across the membrane in order selectively to influence the transport of substances through the membrane in a desired manner (Membranverfahren [Membrane methods], T. Melin and R. Rautenbach, Springer-Verlag, 2004). Sparingly volatile liquids may also expediently be used as solvent.

For cost reasons, it is always desirable to minimize the amount of entrainer to be used in extractive rectification or the amount of solvent to be used in liquid-liquid extraction or a membrane method and to recycle it to the separation process after purification.

Problems occur if, for example in a purification rectification associated with extractor rectification or liquid-liquid extraction or the membrane method, a sparingly volatile entrainer or sparingly volatile solvent has to be freed from all more readily volatile impurities. Usually, complete purification of the entrainer or solvent is necessary since residues of readily volatile impurities hinder the main separation process. The sparingly volatile liquids cannot be purified to any desired high purities since there would then no longer be any fluids at all in the bottom of the column which would have a vapor pressure which could be utilized for evaporation. Since in this case only the sparingly volatile component would be present in the bottom of the column, it would be necessary to set either temperatures which are so high as to be technically unrealizable and/or pressures which are so low so as to be technically unrealizable. The abovementioned patents accordingly explain "regeneration of the entrainers ( . . . ) by a stripping column. Since the vapor pressure of the (pure) entrainer ( . . . ) and hence also its partial pressure in the mixture with the bottom product are zero, the entrainer ( . . . ) cannot be freed completely of the bottom product by pure evaporation in the counter-current process." (DE 10136614 A1, page 3, line 60 et seq., DE 10160518 A1, page 4, line 19 et seq., EP 1372807 B1, page 10, line 46 et seq.).

The same problem arises in a (one-stage) distillation, evaporation or flashing for freeing the sparingly volatile component of all more readily volatile impurities. In Chemical & Engineering News (American Chemical Society) of Apr. 29, 2002, page 4, Prof. Albrecht Salzer writes "that IL (ionic liquids) cannot be distilled, which would be a simple way of recycling, but have to be extracted with organic solvents".

Analogous problems arise in chemical reactions which are carried out in sparingly volatile fluids (e.g. ionic liquids) e.g. described in: "Ionic Liquids in Synthesis" (P. Wasserscheid and T. Welton, Wiley-VCH, ISBN 3-527-30515-7). Here, various volatile substances, in particular reaction products, have to be separated from the sparingly volatile fluids. The more successful the separation of the products, the higher is the direct yield and the greater is the conversion on re-using the recycled solvent in equilibrium reactions.

In the abovementioned and further publications (e.g. WO A 99/41752, US 2003 0085156 A), in which sparingly volatile fluids are used as selective additives for the separation of substances, known alternative methods for freeing the sparingly volatile fluids from impurities are proposed, but without discussing them explicitly, e.g. according to thermophysical properties of the substances involved:
  stripping with vapors or gasses
  extraction with liquids or supercritical gasses
  fractional crystallization/precipitation of individual components
  electrolysis/electrochemistry
  preparative chromatography
  chemical reactions before separation WO A 2001 15175 describes a method for purifying ionic liquids in which the liquids to be purified are thermally decomposed at low pressure and the decomposition products are purified and are reacted back to give the ionic liquid again. However, losses of product occur. In addition, the preparation of ionic liquids and hence also the reconversion of them from the decomposition products are extremely expensive.

It is known to the person skilled in the art that both the use of auxiliaries to be removed again or optionally to be purified (stripping, extraction), the handling of solids (crystallization, electrolysis, chromatography) and the use of chemical reactions are associated with considerable effort, which is to be avoided.

Accordingly, the use of sparingly volatile fluid is currently limited by virtue of the fact that no industrially suitable purification methods are available.

DETAILED DESCRIPTION OF THE INVENTION

Starting from the prior art, it is therefore the object to provide a method which permits, in a simple manner and on an industrial scale, the purification of sparingly volatile fluids to remove more readily volatile components and which has process engineering advantages and is economical.

Figure 1:
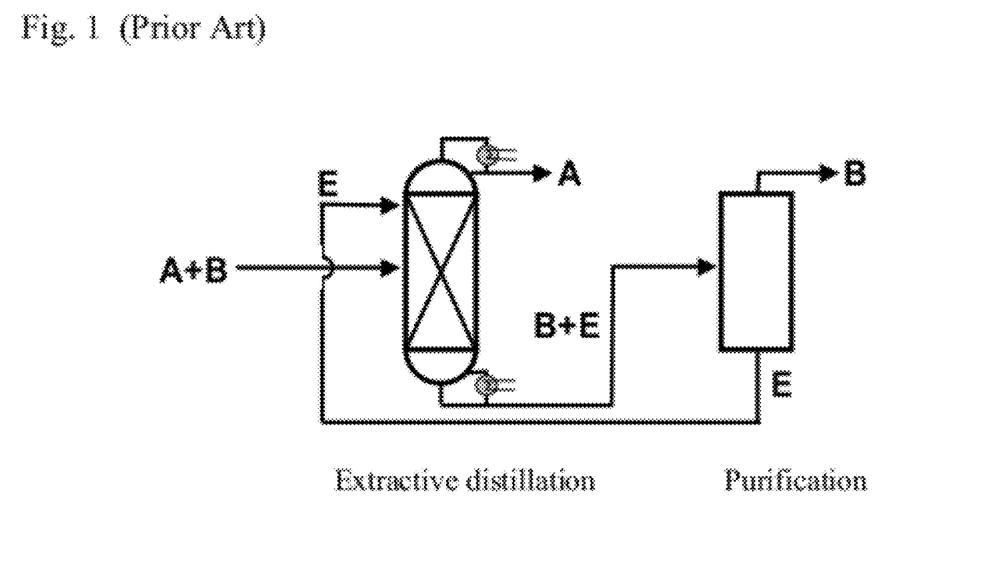
FIG. 1 shows the diagram of an extractive distillation for separating the mixture A+B with purification and recycling of the entrainer "E".

The problem is explained here with reference to an example which it has not been possible to solve satisfactorily to date and which was solved by the method according to the invention. A description is limited here to the substantial aspects of a separation of a mixture of substances A+B, described in the prior art in DE 10136614 A1, EP 1372807 B1 and DE 10160518 A1 (cf. FIG. 1):

In the extractive distillation considered, a sparingly volatile entrainer E in which the component B has substantially better solubility than the component A is added at the top of the column so that component A is obtained at the top of the column and component B and the entrainer E leave the column together at the bottom. In a second step, component B must now be separated from the entrainer so that the entrainer can be recycled to the column and pure product B is obtained. It is of interest here that both component B and the entrainer are obtained in high purity. If the entrainer were to contain significant amounts of component B, the component B present would contaminate the top product (pure A) on recycling to the top of the column. Owing to the abovementioned considerable effort in the separation by other separation methods, a rectification for separating entrainer and component B in the second step would be desirable or would even be necessary in the interest of an economical process. The reasons mentioned in DE 10136614 A1, page 3, line 60 et seq., DE 10160518 A1, page 4, line 19 et seq., EP 1372807 B1, page 10, line 46 et seq. or by Prof. Albrecht Salzer, Chemical & Engineering News of Apr. 29, 2002, page 4, appear, however, to prevent this use.

The present invention therefore relates to a method for separating one or more volatile components from one or more sparingly volatile fluids by multi-stage rectification using at least one volatile auxiliary, characterized in that the auxiliary used or the auxiliary mixture in the bottom of the distillation unit contributes a significant proportion to the pressure owing to its partial pressure and the pressure in the bottom of the column minus the partial pressure of the auxiliary or of the auxiliary mixture which prevails there does not exceed 10 mbar and the auxiliary used or the auxiliary mixture leaves the distillation unit for the most part together with sparingly volatile fluids at the bottom.

The auxiliary used, individual or as a mixture, contributes a significant proportion to the vapor pressure through its vapor pressure in the bottom of the column, the significant proportion being at least 50%, preferably at least 75%, particularly preferably at least 90%, so that the freeing of the sparingly volatile substance by means of rectification under technically expedient conditions from all volatile impurities to be removed (with the exception of the auxiliary) is possible and the problem of the limited purification described above and in DE 10136614 A1 and DE 10160518 A1 and EP 1372807 B1 can be solved in a surprisingly simple manner.

In the bottom of the distillation column, the partial pressure of the auxiliary or of the auxiliary mixture is higher than the pressure there of the components to be removed as impurities via the top.

The pressure in the bottom of the column minus the partial pressure of the auxiliary or the auxiliary mixture prevailing there is not more than 10 bar, preferably not more than 5 mbar, particularly preferably not more than 2 mbar, in the method according to the invention.

According to the invention, the auxiliary or the auxiliary mixture is to leave the purification column together with the sparingly volatile fluid, for the most part at the bottom of the purification column, "for the most part" being understood as meaning at least 50% by weight, preferably at least 75% by weight, particularly preferably at least 95% by weight. The major part of the more readily volatile impurities leaves the purification column at the top.

The amount of the auxiliary used, individually or as a mixture, depends on economic and thermodynamic points of view and on the type of use; based on the bottom stream of the purification column, it may be less than 40% by weight, preferably less than 20% by weight, very particularly preferably less than 10% by weight, in a preferred embodiment of the method according to the invention where there is as complete purification as possible of the sparingly volatile fluid.

In a either embodiment in the case of, for example, a purification of a sparingly volatile liquid with starting material as auxiliary, which purification is associated with a chemical reaction, the amount of auxiliary can be as large as desired since at the starting material would enter the reaction again on recycling the purified sparingly volatile fluid. The pure-substance vapor pressure of the auxiliary or of the auxiliary mixture at operating temperature is substantially greater than that of the sparingly volatile fluid and is so by a factor of at least 10, preferably by a factor of at least 100, particularly preferably by a factor of at least 1000, the pure-substance vapor pressure of the sparingly volatile fluid at bottom temperature being as a rule below 5 mbar. Auxiliaries which are used above their critical temperature have—analogously—a higher vapor pressure than the sparingly volatile fluid at their critical temperature.

Figure 2:
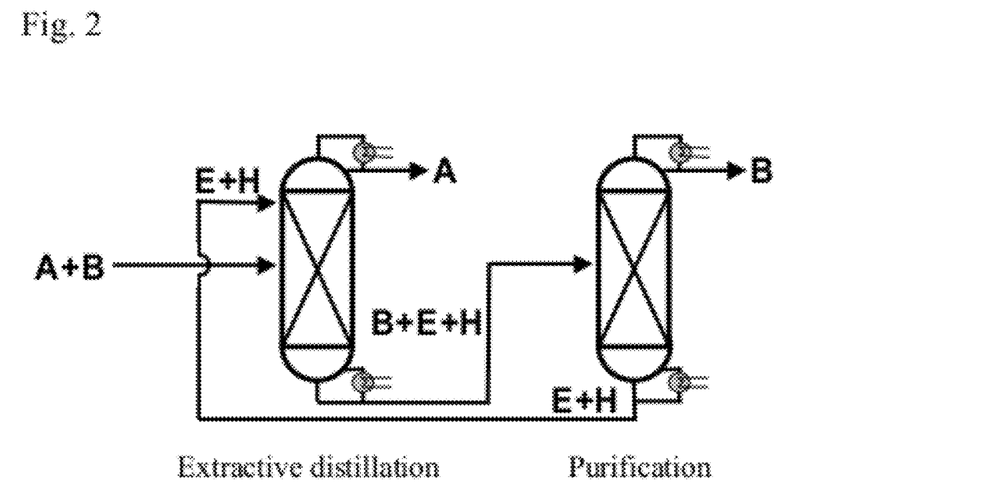
FIG. 2 shows the diagram of an extractive distillation for separating the mixture A+B with purification and recycling of the entrainer E with the aid of the auxiliary "H", which is likewise recycled.

Without wishing to limit the general usability of the invention thereto, the solution of the problem described by way of example is explained by the method according to the invention (cf. FIG. 2).

According to the invention, in the extractive distillation described, an auxiliary H is circulated together with the entrainer E, leaves the extractive distillation column together with the entrainer E and the product B at the bottom and permits, in a second column, the purification column, the isolation of the product B which leaves the purification column at the top, which auxiliary then emerges together with the entrainer at the bottom. Entrainer and auxiliary are then added again at the top of the extractive distillation column. Via the design of the purification column, especially column height and reflux ratio, the amount of the impurity B in the recycled entrainer can then be reduced as desired without having the problems explained above.

The method according to the invention has the advantages that, with a suitable choice of the auxiliary, the latter need be metered only in low concentrations and it nevertheless permits technically expedient conditions (high pressure, low temperature) in the evaporator, that it can be separated readily from the top product in the purification column, that—where the purification method according to the invention is associated with a separation method—it doesn't have to be subsequently separated from the sparingly volatile substance because it does not significantly disturb the remaining process in the concentration used, that, in a corresponding problem, it can be circulated so that the costs of the auxiliary are reduced and that in the case of a corresponding problem, it can be circulated with the sparingly volatile substance in order to be able to combine a plurality of the abovementioned advantages.

The method according to the invention obviously differs from the classical steam distillation method, in which a low boiling point is achieved by addition of the auxiliary water, in that the auxiliary added here is used only in small amounts and it leaves the distillation unit, in which it acts as an auxiliary, virtually exclusively through the bottom. Since the basis of steam distillation is the immiscibility of the water with the components to be evaporated in order to increase the total pressure, it is moreover incorrect to infer from the steam distillation the invention made here, since the latter is indeed not dependent on this effect.

The method according to the invention obviously differs from the classical stripping method, in which a vapor phase is produced in the distillation by addition of an auxiliary as a gas or vapor, in that the auxiliary added here leaves this distillation substantially at the bottom while, during stripping, the auxiliary leaves the distillation substantially at the top. Since the principle of stripping is precisely that the auxiliary leaves the distillation substantially at the top, it is moreover incorrect to infer from stripping the invention made here, since the latter is so to speak the opposite in this respect.

The distillate purification method according to the invention differs from the extractive distillations in that, with a postulated chemical and thermal stability of the components in the case of a similar number of theoretical plates, similarly complete separation of the volatile components from the sparingly volatile fluid could be achieved without an auxiliary if the operating pressure were to be lowered or the operating temperature raised i.e. by virtue of the fact that an entrainer in the extractive distillation significantly changes in the intended manner the relative volatility of the components to be separated, which is not necessary with the use of the auxiliary in the distillation according to the invention.

The sparingly volatile fluids to be purified by the method according to the invention are pure chemical compounds or mixtures which, at operating temperature of the purification process, have vapor pressures below 10 mbar, preferably below 1 mbar, particularly preferably below 0.1 mbar. The operating temperature is usually a temperature at which no troublesome decomposition reactions or the like occur; this will as a rule be a temperature below 600° C., preferably below 350° C., particularly preferably below 200° C.

The sparingly volatile fluids may be in particular ionic liquids, as defined by P. Wasserscheid and W. Keim in Angewandten Chemie, 2000, 112, 3926-3945, individually or as mixtures, or mixtures of one or more polymers with one or more ionic liquids or mixtures of one or more sparingly volatile fluids with one or more ionic liquids. In comparison with conventional salts, ionic liquids are liquid at substantially lower temperatures (as a rule below 200° C.) and frequently have a melting point below 0° C., in individual cases down to −96° C., which is important for, for example, the industrial implementation of the extractive rectification. In addition, ionic liquids are as a rule non-flammable and non-corrosive and not very viscous and are distinguished as a rule by a low vapor pressure, which is currently not measurable in some cases. They frequently have very good solubilities for a large number of organic, inorganic and polymeric substances.

Preferably considered ionic liquids are those—or the ions thereof—which are mentioned in one or more of the following publications or literature references cited there: EP 1372807 B1, DE 10154052 A1, DE 10206808 A1, WO 03/037835 A3, WO A 2002 074718, U.S. Pat. Nos. 6,339,182 B1, 4,359,596 B, 5,220,106 B, DE 19901524 A1, WO A 00/16902, WO A1 01/98239, WO A1 03/051894, WO A1 03/062251, DE A1 19919494, "Ionic Liquids in Synthesis" ISBN 3527305157, "Molten Salt Techniques" ISBN 0306435543, "Ionic Liquids" ISBN 0841237891, "Ionic Liquids as Green Solvents" ISBN 0841238561, "Green Industrial Applications of Ionic Liquids" ISBN 1402011377, Chem. Rev. 1999, 99, 2071-2083.

According to the invention, ionic liquids are designated as those compounds which have at least one positive and at least one negative charge but are charge-neutral overall, and have a melting point below 200° C., preferably below 100° C., particularly preferably below 50° C.

The ionic liquids may also have a plurality of positive or negative charges, for example from 1 to 5, preferably from 1 to 4, particularly preferably from 1 to 3, very particularly preferably 1 or 2, but in particular one positive and one negative charge each. The charges may be present on different localized or delocalized regions within a molecule, i.e. in a betaine-like manner, or may be distributed over a separate anion and a separate cation. Those ionic liquids which are composed of at least one cation and at least one anion are preferred. As mentioned above, cation and anion may have one or more charges, preferably one charge.

Preferred cations are ammonium or phosphonium ions or those cations which contain at least one five- or six-membered heterocycle which has at least one phosphorous or nitrogen atom and optionally an oxygen or sulfur atom, particularly preferably those compounds which contain at least one five- or six-membered heterocycle which has one, two or three nitrogen atoms and a sulfur or an oxygen atom, very particularly preferably those having one or two nitrogen atoms.

Particularly preferred ionic liquids are those which have a molecular weight below 1000 g/mol, very particularly preferably below 350 g/mol.

Other preferred cations are those which are selected from the compounds of the formulae 1 to 23.

1

2

3

4

5

6

-continued

7

8

9

10

11

12

13

14

15

16

-continued

17

18

19

20

21

22

23 and oligomers or polymers which contain these structures, in which $R^1$, $R^2$, $R^3$, $R^4$, $R^5$, $R^6$ and $R^7$, independently of one another are each $C_1$-$C_{18}$-alkyl, $C_2$-$C_{18}$-alkyl optionally interrupted by one or more oxygen and/or sulfur atoms and/or one or more substituted or unsubstituted imino groups, $C_{12}$-$C_{18}$-alkyl, $C_6$-$C_{12}$-aryl, $C_5$-$C_{12}$-cycloalkyl or a five- or six-membered heterocycle having oxygen, nitrogen and/or sulfur atoms, or two of them together form an unsaturated, saturated or aromatic ring optionally substituted by one or more oxygen and/or sulfur atoms and/or one or more substituted or unsubstituted imino groups, it being possible for said radicals in each case to be substituted by functional groups, aryl, alkyl, aryloxy, alkoxy, halogen, heteroatoms and/or heterocycles.

$R^1$, $R^2$, $R^3$, $R^4$, $R^5$ and $R^6$ may additionally be hydrogen.

$R^7$ may moreover be $C_1$-$C_{18}$-alkyloyl (alkylcarbonyl), $C_1$-$C_{18}$-alkoxycarbonyl, $C_5$-$C_{12}$-cycloalkylcarbonyl or $C_6$-$C_{12}$-aryloyl (arylcarbonyl), it being possible for said radicals in each case to be substituted by functional groups, aryl, alkyl, aryloxy, alkoxy, halogen, heteroatoms and/or heterocycles.

$C_1$-$C_{18}$-alkyl optionally substituted by functional groups, aryl, alkyl, aryloxy, alkoxy, halogen, heteroatoms and/or heterocycles is, for example, methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, hetadecyl, octadecyl, 1,1-dimethylpropyl, 1,1-dimethylbutyl, 1,1,3,3-tetramethylbutyl, benzyl, 1-phenylethyl, 2-phenylethyl, α,α-dimethylbenzyl, benzhydryl, p-tolylmethyl, 1-(p-butylphenyl)ethyl, p-chlorobenzyl, 2,4-dichlorobenzyl, p-methoxybenzyl, m-ethoxybenzyl, 2-cyanoethyl, 2-cyanopropyl, 2-methoxycarbonethyl, 2-ethoxycarbonylethyl, 2-butoxycarbonylpropyl, 1,2-di(methoxycarbonyl)ethyl, 2-methoxyethyl, 2-ethoxyethyl, 2-butoxyethyl, diethoxymethyl, diethoxyethyl, 1,3-dioxan-2-yl, 2-methyl-1,3-dioxolan-2-yl, 4-methyl-1,3-dioxolan-2-yl, 2-isopropoxyethyl, 2-butoxypropyl, 2-octyloxyethyl, chloromethyl, 2-chloroethyl, trichloromethyl, trifluoromethyl, 1,1-dimethyl-2-chloroethyl, 2-methoxyisopropyl, 2-ethoxyethyl, butylthiomethyl, 2-dodecylthioethyl, 2-phenylthioethyl, 2,2,2-trifluoroethyl, 2-hydroxyethyl, 2-hydroxypropyl, 3-hydroxypropyl, 4-hydroxybutyl, 6-hydroxyhexyl, 2-aminoethyl, 2-aminopropyl, 3-aminopropyl, 4-aminobutyl, 6-aminohexyl, 2-methylaminoethyl, 2-methylaminopropyl, 3-methylaminopropyl, 4-methylaminobutyl, 6-methylaminohexyl, 2-dimethylaminoethyl, 2-dimethylaminopropyl, 3-dimethylaminopropyl, 4-dimethylaminobutyl, 6-dimethylaminohexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl and $C_2$-$C_{18}$-alkyl optionally interrupted by one or more oxygen and/or sulfur atoms and/or one or more substituted or unsubstituted imino groups is, for example, 5-hydroxy-3-oxapentyl, 8-hydroxy-3,6-dioxaoctyl, 11-hydroxy-3,6,9-trioxaundecyl, 7-hydroxy-4-oxaheptyl, 11-hydroxy-4,8-dioxaundecyl, 15-hydroxy-4,8,12-trioxapentadecyl, 9-hydroxy-5-oxanonyl, 14-hydroxy-5,10-oxatetradecyl, 5-methoxy-3-oxapentyl, 8-methoxy-3,6-dioxaoctyl, 11-methoxy-3,6,9-trioxaundecyl, 7-methoxy-4-oxaheptyl, 11-methoxy-4,8-dioxaundecyl, 15-methoxy-4,8,12-trioxapentadecyl, 9-methoxy-5-oxanonyl, 14-methoxy-5,10-oxatetradecyl, 5-ethoxy-3-oxapentyl, 8-ethoxy-3,6-dioxaoctyl, 11-ethoxy-3,6,9-trioxaundecyl, 7-ethoxy-4-oxaheptyl, 11-ethoxy-4,8-dioxaundecyl, 15-ethoxy-4,8,12-trioxapentadecyl, 9-ethoxy-5-oxanonyl or 14-ethoxy-5,10-oxatetradecyl.

If two radicals form a ring, these radicals together may be 1,3-propylene, 1,4-butylene, 2-oxa-1,3-propylene, 1-oxa-1,3-propylene, 2-oxa-1,3-propylene, 1-oxa-1,3-propenylene, 1-aza-1,3-propenylene, 1-$C_1$-$C_4$-alkyl-1-aza-1,3-propenylene, 1,4-buta-1,3-dienylene, 1-aza-1,4-buta-1,3-dienylene or 2-aza-1,4-buta-1,3-dienylene.

The number of oxygen and/or sulfur atoms and/or imino groups is not limited. As a rule, it is not more than 5 in the radical, preferably not more than 4 and very particularly preferably not more than 3.

Furthermore, as a rule at least one carbon atom is present between two heteroatoms, preferably at least two carbon atoms are present between two heteroatoms.

Substituted and unsubstituted imino groups may be, for example, imino, methylimino, isopropylimino, n-butylimino or tert-butylimino.

Furthermore
- functional groups are, for example, carboxyl, carboxamido, hydroxyl, di($C_1$-$C_4$-alkyl)amino, $C_1$-$C_4$-alkoxycarbonyl, cyano or $C_1$-$C_4$-alkoxy,
- $C_6$-$C_{12}$-aryl optionally substituted by functional groups, aryl, alkyl, aryloxy, alkoxy, halogen, heteroatoms and/or heterocycles is, for example, phenyl, tolyl, xylyl, α-naphthyl, β-naphthyl, 4-biphenylyl, chlorophenyl, dichlorophenyl, trichlorophenyl, difluorophenyl, methylphenyl, dimethylphenyl, trimethylphenyl, ethylphenyl, diethylphenyl, iso-propylphenyl, tert-butylphenyl, dodecylphenyl, methoxyphenyl, dimethoxyphenyl, ethoxyphenyl, hexyloxyphenyl, methylnaphthyl, iso-propylnaphthyl, chloronaphthyl, ethoxynaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, methoxyethylphenyl or ethoxymethylphenyl,
- $C_5$-$C_{12}$-cycloalkyl optionally substituted by functional groups, aryl, alkyl, aryloxy, alkoxy, halogen, heteroatoms and/or heterocycles is, for example, cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl and a saturated or unsaturated bicyclic system, such as, for example, norbornyl or norbornenyl,
- a five- or six-membered heterocycle having oxygen, nitrogen and/or sulfur atoms is, for example, furyl, thiophenyl, pyrryl, pyridyl, indolyl, benzoxazolyl, dioxolyl, dioxyl, benzimidazolyl, benzothiazolyl, dimethylpyridyl, methylquinolyl, dimethylpyrryl, methoxyfuryl, dimethoxypyridyl, difluorpyridyl, methylthiophenyl, isopropylthiophenyl or tert-butylthiophenyl and
- $C_1$ to $C_4$-alkyl is, for example, methyl, ethyl, propyl, iso-propyl, n-butyl, sec-butyl or tert-butyl.

$C_1$-$C_{18}$-alkyloyl (alkylcarbonyl) is, for example, acetyl, propionyl, n-butyloyl, sec-butyloyl, tert-butyloyl, 2-ethylhexylcarbonyl, decanoyl, dodecanoyl, chloroacetyl, trichloroacetyl or trifluoroacetyl.

$C_1$-$C_{18}$-alkoxycarbonyl is, for example, methoxycarbonyl, ethoxycarbonyl, propoxycarbonyl, isopropoxycarbonyl, n-butoxycarbonyl, sec-butoxycarbonyl, tert-butoxycarbonyl, hexyloxycarbonyl, 2-ethylhexyloxycarbonyl or benzyloxycarbonyl.

$C_5$-$C_{12}$-cycloalkylcarbonyl is, for example, cyclopentylcarbonyl, cyclohexylcarbonyl or cyclododecylcarbonyl.

$C_6$-$C_{12}$-aryloyl (arylcarbonyl) is, for example, benzoyl, toluoyl, xyloyl, α-naphthoyl, β-naphthoyl, chlorobenzoyl, dichlorobenzoyl, trichlorobenzoyl or trimethylbenzoyl.

$R^1$, $R^2$, $R^3$, $R^4$, $R^5$ and $R^6$, independently of one another, are preferably hydrogen, methyl, ethyl, n-butyl, 2-hydroxyethyl, 2-cyanoethyl, 2-(methoxycarbonyl)ethyl, 2-(ethoxycarbonyl)ethyl, 2-(n-butoxycarbonyl)ethyl, dimethylamino, diethylamino and chlorine.

$R^7$ is preferably methyl, ethyl, n-butyl, 2-hydroxyethyl, 2-cyanoethyl, 2-(methoxycarbonyl)ethyl, 2-(ethoxycarbonyl)ethyl, 2-(n-butoxycarbonyl)ethyl, acetyl, propionyl, tert-butyryl, methoxycarbonyl, ethoxycarbonyl or n-butoxycarbonyl.

Particularly preferred pyridinium ions corresponding to formula 1 are those in which at least one of the radicals $R^1$ to $R^5$ is methyl, ethyl or chlorine, $R^7$ is acetyl, methyl, ethyl or n-butyl and all others are hydrogen, or $R^3$ is dimethylamino, $R^7$ is acetyl, methyl, ethyl or n-butyl and all others are hydrogen, or $R^7$ is acetyl, methyl, ethyl or n-butyl and all others are hydrogen, or $R^2$ is carboxyl or carboxamido, (and?) $R^7$ is acetyl, methyl, ethyl or n-butyl and all others are hydrogen, or $R^1$ and $R^2$ or $R^2$ and $R^3$ are 1,4-buta-1,3-dienylene, $R^7$ is acetyl, methyl, ethyl or n-butyl and all others are hydrogen.

Particularly preferred pyridazinium ions corresponding to formula 2 are those in which one of the radicals $R^1$ to $R^4$ is methyl or ethyl, $R^7$ is acetyl, methyl, ethyl or n-butyl and all others are hydrogen, or $R^7$ is acetyl, methyl, ethyl or n-butyl, and all others are hydrogen.

Particularly preferred pyrimidinium ions corresponding to formula 3 are those in which $R^2$ to $R^4$ are hydrogen or methyl, $R^7$ is acetyl, methyl, ethyl or n-butyl and $R^1$ is hydrogen, methyl or ethyl, or $R^2$ and $R^4$ are methyl, $R^3$ is hydrogen and $R^1$ is hydrogen, methyl or ethyl and $R^7$ is acetyl, methyl, ethyl or n-butyl.

Particularly preferred pyrazinium ions corresponding to formula 4 are those in which
$R^1$ to $R^4$ are all methyl and
$R^7$ is acetyl, methyl, ethyl or n-butyl or $R^7$ is acetyl, methyl, ethyl or n-butyl and all others are hydrogen.

Particularly preferred imidazolium ions corresponding to formula 5 are those in which, independently of one another,
$R^1$ is selected from the group consisting of methyl, ethyl, n-propyl, n-butyl, n-pentyl, n-octyl, n-decyl, n-dodecyl, 2-hydroxyethyl or 2-cyanoethyl,
$R^7$ is acetyl, methyl, ethyl or n-butyl and
$R^2$ to $R^4$ independently of one another, are hydrogen, methyl or ethyl.

Particularly preferred 1H-pyrazolium ions corresponding to formula 6 are those in which, independently of one another,
$R^1$ is hydrogen, methyl or ethyl,
$R^2$, $R^3$ and $R^4$ are hydrogen or methyl and
$R^7$ is acetyl, methyl, ethyl or n-butyl.

Particularly preferred 3H-pyrazolium ions corresponding to formula 7 are those in which, independently of one another,
$R^1$ is hydrogen, methyl or ethyl,
$R^2$, $R^3$ and $R^4$ are hydrogen or methyl and
$R^7$ is acetyl, methyl, ethyl or n-butyl.

Particularly preferred 4H-pyrazolium ions corresponding to formula 8 are those in which, independently of one another,
$R^1$ to $R^4$ are hydrogen or methyl and
$R^7$ is acetyl, methyl, ethyl or n-butyl.

Particularly preferred 1-pyrazolinium ions corresponding to formula 9 are those in which, independently of one another,
$R^1$ to $R^6$ are hydrogen or methyl and
$R^7$ is acetyl, methyl, ethyl or n-butyl.

Particularly preferred 2-pyrazolinium ions corresponding to formula 10 are those in which, independently of one another,
$R^1$ is hydrogen, methyl, ethyl or phenyl,
$R^7$ is acetyl, methyl, ethyl or n-butyl and
$R^2$ to $R^6$ is hydrogen or methyl.

Particularly preferred 3-pyrazolinium ions corresponding to formula 11 are those in which, independently of one another,
$R^1$ or $R^2$ is hydrogen, methyl, ethyl or phenyl,
$R^7$ is acetyl, methyl, ethyl or n-butyl and
$R^3$ to $R^6$ are hydrogen or methyl.

Particularly preferred imidazolinium ions corresponding to formula 12 are those in which, independently of one another,
$R^1$ or $R^2$ is hydrogen, methyl, ethyl, n-butyl or phenyl,
$R^7$ is acetyl, methyl, ethyl or n-butyl and
$R^3$ or $R^4$ is hydrogen, methyl or ethyl and
$R^5$ or $R^6$ is hydrogen or methyl.

Particularly preferred imidazolinium ions corresponding to formula 13 are those in which, independently of one another, $R^1$ or $R^2$ is hydrogen, methyl or ethyl,
$R^7$ is acetyl, methyl, ethyl or n-butyl and
$R^3$ to $R^6$ is hydrogen or methyl.

Particularly preferred imidazolinium ions corresponding to formula 14 are those in which, independently of one another, $R^1$, $R^2$ or $R^3$ is hydrogen, methyl or ethyl,
$R^7$ is acetyl, methyl, ethyl or n-butyl and
$R^4$ to $R^6$ are hydrogen or methyl.

Particularly preferred thiazolium ions corresponding to formula 15 or oxazolium ions corresponding to formula 16 are those in which, independently of one another, $R^1$ is hydrogen, methyl, ethyl or phenyl,
$R^7$ is acetyl, methyl, ethyl or n-butyl and
$R^2$ or $R^3$ is hydrogen or methyl.

Particularly preferred 1,2,4-triazolium ions corresponding to formulae 17 and 18 are those in which, independently of one another, $R^1$ or $R^2$ is hydrogen, methyl, ethyl or phenyl,
$R^7$ is acetyl, methyl, ethyl or n-butyl and
$R^3$ is hydrogen, methyl or phenyl.

Particularly preferred 1,2,3-triazolium ions corresponding to formulae 19 and 20 are those in which, independently of one another, $R^1$ is hydrogen, methyl or ethyl,
$R^7$ is acetyl, methyl, ethyl or n-butyl and
$R^2$ or $R^3$ is hydrogen or methyl or
$R^2$ and $R^3$ are 1,4-buta-1,3-dienylene and all others are hydrogen.

Particularly preferred pyrrolidinium ions corresponding to formula 21 are those in which, independently of one another, $R^1$ and $R^7$ are acetyl, methyl, ethyl or n-butyl and
$R^2$, $R^3$, $R^4$ and $R^5$ are hydrogen.

Particularly preferred ammonium ions corresponding to formula 22 are those in which, independently of one another, $R^7$ is acetyl, methyl, ethyl or n-butyl and
$R^1$, $R^2$, and $R^3$ are methyl, ethyl, n-butyl, 2-hydroxyethyl, benzyl or phenyl.

Particularly preferred phosphonium ions corresponding to formula 23 are those in which, independently of one another $R^7$ is acetyl, methyl, ethyl or n-butyl and
$R^1$, $R^2$, and $R^3$ are phenyl, phenoxy, ethoxy and n-butoxy.

Among these, the ammonium, phosphonium, pyridinium and imidazolinium ions are preferred.

Very particularly preferred cations are 1,2-dimethylpyridinium, 1-methyl-2-ethylpyridinium, 1-methyl-2-ethyl-6-methylpyridinium, N-methylpyridinium, 1-butyl-2-methylpyridinium, 1-butyl-2-ethylpyridinium, 1-butyl-2-ethyl-6-methylpyridinium, n-butylpyridinium, 1-butyl-4-methylpyridinium, 1,3-dimethylimidazolium, 1,2,3-trimethylimidazolium, 1-n-butyl-3-methylimidazolium, 1,3,4,5-tetramethylimidazolium, 1,3,4-trimethylimidazolium, 2,3-dimethylimidazolium, 1-butyl-2,3-dimethylimidazolium, 3,4-dimethylimidazolium, 2-ethyl-3,4-dimethylimidazolium, 3-methyl-2-ethylimidazol, 3-butyl-1-methylimidazolium, 3-butyl-1-ethylimidazolium, 3-butyl-1,2-dimethylimidazolium, 1,3-di-n-butylimidazolium, 3-butyl-1,4,5-trimethylimidazolium, 3-butyl-1,4-dimethylimidazolium, 3-butyl-2-methylimidazolium, 1,3-dibutyl-2-methylimidazolium, 3-butyl-4-methylimidazolium, 3-butyl-2-ethyl-4-methylimidazolium and 3-butyl-2-ethylimidazolium, 1-methyl-3-octylimidazolium, 1-decyl-3-methylimidazolium.

1-butyl-4-methylpyridinium, 1-n-butyl-3-methylimidazolium and 1-n-butyl-3-ethylimidazolium are particularly preferred.

Conceivable anions are in principle whole anions.

Preferred anions are halides, $F^-$, $Cl^-$, $Br^-$, $I^-$, acetate $CH_3COO^-$, trifluoroacetate $CF_3COO^-$, triflate $C_3SO_3^-$, sulfate $SO_4^{2-}$, hydrogen sulfate $HSO_4^-$, methyl sulfate $CH_3OSO_3^-$, ethyl sulfate, $C_2H_5OSO_3^-$, sulfite $SO_3^{2-}$, hydrogen sulfite $HSO_3^-$, aluminum chloride $AlCl_4^-$, $Al_2Cl_7^-$, $Al_3Cl_{10}^-$, aluminum tetrabromide $AlBr_4-$, nitrite $NO_2^-$, nitrate $NO_3^-$, copper chloride $CuCl_2^-$, phosphate $PO_4^{3-}$, hydrogen phosphate $HPO_4^{2-}$, dihydrogen phosphate $H_2PO_4^-$, carbonate $CO_3^{2-}$, bicarbonate $HCO_3^-$.

Tetrafluoroborate $BF_4^-$, hexafluorophosphate $PF_6^-$, bis (trifluoromethylsulfonyl)imide $(CF_3 \ SO_2)_2N^-$, tosylate p-$CH_3C_6H_4SO_3^-$ are particularly preferred.

Among the ionic liquids, very particularly preferred ones are those whose salts have an $E_T(30)$-value of >20, preferably of >30, particularly preferably of >40. The $E_T(30)$ value is a measure of the polarity and is described by C. Reichardt in Reichardt, Christian Solvent Effects in Organic Chemistry, Weinheim: VCH, 1979.-XI, (Monographs in Modern Chemistry; 3), ISBN 3-527-25793-4 page 241.

The sparingly volatile fluids according to the invention may also be polymers. Here, the polymers may have any desired polymer architecture preferably linear, branched or hyperbranched as homopolymers or as alternating, random or gradient copolymers, as graft, comb or block copolymers, particularly preferably hyperbranched as homopolymers or as alternating, random or gradient copolymers. Hyperbranched polymers are understood as meaning those as defined by Kim, Y. H. (in Journal of Polymer Science, Part A: Polymer Chemistry, 1998, 36, 1685) and Hult, A., Johannson, M., Malmström, E. (in Advances in Polymer Science, 1999, 143) and/or Arlt et al. (in DE 10160518 AI). The polymers used preferably have a molar mass of from 800 g/mol to 500 000 g/mol, particularly preferably from 1000 g/mol to 50 000 g/mol, and may have, as functional groups, those groups which are mentioned in Lehrbuch der Organischen Chemie (H. Beyer and W. Walter; S. Hirzel Verlag Stuttgart, 21st edition; 1988)—preferably OH, carbonyl, carboxyl, amino, mercapto, or nitro groups—alone or side by side. The polymers used can be selected, inter alia, from the polymers mentioned in Lehrbuch der Organischen Chemie (H. Beyer and W. Walter; S. Hirzel Verlag Stuttgart, 21st edition; 1988) and/or DE10160518A1—preferably polyethers, aliphatic polyesters, polyglycerols, polyphenylenes, polypropylenimine, polyamidoamine or poly(meth)acrylic acid derivates and can be used individually or as mixtures.

The sparingly volatile fluid may also be polymer blends or mixtures of one or more polymers with one or more ionic liquids or mixtures of one or more sparingly volatile fluids with one or more polymers.

Absorbents or emulsions or suspensions with sparingly volatile fluids are also conceivable. It would also be possible to treat the flowable, e.g. pulverulent or granular, solids which, for example, are contaminated on the surface.

The volatile fluids to be separated off by the method according to the invention are all fluids (in particular liquids or liquefied gasses or permanent gasses) which, in the distillation considered, have a higher partition coefficient $y_i/x_i$ than the sparingly volatile fluid from which these are to be separated.

Volatile components to be separated off in the purification method according to the invention may be for example, but not exclusively:

aromatic and aliphatic hydrocarbons
alkanes and alkenes having from 1 to 12, preferably from 2 to 10, carbon atoms
ketones
amides and acids, preferably carboxylic acids
alcohols, acetates, ethers
sulfides
halohydrocarbons
furans cyclic compounds of the above species
water Auxiliaries used in the method according to the invention may be all fluids which, in the distillation considered, have a higher partition coefficient $y_i/x_i$ than the sparingly volatile fluids with which these are mixed but at the same time have a partition coefficient which is usually lower than the partition coefficient of the volatile component or the components to be removed.

In a preferred embodiment of the method, auxiliaries used in the method according to the invention are chemically substantially inert. However, depending on the type of use—other possible auxiliaries are of course those which, when used/reused in an associated separation method, additionally advantageously influence the activity coefficient of the fluids to be separated and/or perform a function in an associated chemical reaction when used/reused.

Regarding the chemical structure of the auxiliaries to be used and components A and B to be separated, there are no general limitations provided that they are thermally sufficiently stable and have the properties required elsewhere here with regard to the partial pressures and vapor pressure. Preferred chemical compounds are those which are known from textbooks and/or reference works of chemistry and/or engineering sciences, inter alia all chemical compounds whose name or group is mentioned in one or more of the following literature sources: "Lehrbuch der Organischen Chemie" [Textbook of Organic Chemistry] ISBN 3777604380, "Lehrbuch der Organischen Chemie" [Textbook of Organic Chemistry] ISBN 3527260676, "Lehrbuch der Anorganischen Chemie" [Textbook of Inorganic Chemistry] ISBN 3110075113 and "Ullmann's Encyclopedia of Industrial Chemistry" ISSN 14356007, Beilstein, Gmelin, DE 10136614, EP 1372807 and DE 10160518. Another conceivable auxiliary is a substance which develops the required properties—for example by thermal decomposition or chemical reaction—only within the rectification (e.g. a sparingly volatile auxiliary which, at the bottom temperature, liberates a more volatile auxiliary which leads to a certain bottom pressure).

According to the invention, rectification is understood as meaning a multi-stage distillation under reflux. Key elements of a rectification column are the evaporator in the bottom, by means of which an ascending vapor stream is produced, and the condenser at the top, by means of which a descending liquid stream is produced. Ascending vapor stream and descending liquid stream are brought into intensive contact on internals. With the use of rectifier section and stripping section, the countercurrent thus produced makes it possible to adjust the compositions of the streams at the top and bottom of the column within wide ranges with the aid of the parameters column height and reflux ratio. Apart from being carried out in a conventional column, a rectification can also be carried out in suitable connected apparatuses and machines. Here, a multi-stage rectification is regarded as being one where one or more equilibrium stages and a partial condenser are present or two or more equilibrium stages and a total condenser are present. Here, equilibrium stages, may be parts of a column or a container which could be operated so that approximately a thermodynamic equilibrium would be possible.

The invention also relates to a separation method in which sparingly volatile fluids are used as special additives, characterized in that the sparingly volatile fluids used as special additives are separated from volatile impurities in one or more associated, i.e. preceding, intermediate and/or subsequent process steps by the method according to the invention.

Preferred separation methods are those in which fluids are separated from one another, particularly preferably extractive rectification or liquid-liquid extraction or membrane methods, very particularly preferably extractive rectification. Extractive rectification is understood as meaning the separation method as described in [Stichlmair, S. and Fair, J., Distillation, ISBN 0-471-25241-7, page 241 et seq.]. However, in an extension of the entrainer mentioned, "entrainer" is understood in this patent as meaning the sparingly volatile fluid which may be present in pure form or as a mixture.

A liquid-liquid extraction is described in [Sattler, K., Thermische Trennverfahren [Thermal Separation Methods], ISBN 3-527-28636-5, chapter 6]. However, in an extension of the solvent mentioned, "solvent" is understood in this patent as meaning a sparingly volatile fluid which may be present in pure form or as a mixture.

Membrane methods such as those which may be used in the context of the separation method according to the invention are described, for example, in Membraneverfahren [Membrane Methods], T. Melin and R. Rautenbach, Springer-Verlag, 2004.

In a preferred variant of the method according to the invention, the auxiliary can be reintroduced into the continuous or batchwise separation method together with the purified sparingly volatile fluid; continuous recycling of the components into the running process is preferred here. Continuous recycling into continuously operated methods is particularly preferred.

In a particularly preferred embodiment of the method according to the invention, the auxiliaries in turn additionally support the separation in that they change the separation factor of the components to be separated so that it differs from 1.

Mixtures to be separated in the separation method according to an embodiment of the invention may be selected, for example, but not exclusively, from
- a mixture which contains one or two or more of the substances designated further above as "more readily volatile" and any desired number of further substances,
- a mixture which contains aromatic and aliphatic, including cyclic, hydrocarbons,
- a mixture which contains alkanes and alkenes having from 3 to 12, preferably from 4 to 10, carbon atoms,
- a mixture which contains ketones and alicyclic compounds,
- a mixture which contains amides and acids, preferably carboxylic acids,
- a mixture which contains alcohols and alkanes,
- a mixture which contains alcohols and aromatics,
- a mixture which contains ketones and alcohols,
- a mixture which contains acetates and ketones,
- a mixture which contains ethers and alkanes,
- a mixture which contains ethers and alkenes,
- a mixture which contains sulfides and ketones,
- a mixture which contains halohydrocarbons and ketones,
- a mixture which contains cyclic ketones and cyclic alcohols,
- a system which, in addition to water, contains alcohols having from 1 to 12, preferably from 1 to 8, particularly preferably from 1 to 5, carbon atoms, organic acids, preferably alkanoic acids, ketones, furans.

The invention also relates to chemical reactions in which at least one sparingly volatile fluid is present, characterized in that this is freed from volatile components in at least one associated process step via the purification method according to the invention.

Chemical reactions are understood as meaning those as described for example, but not exclusively, in "Ionic Liquids in Synthesis" (P. Wasserscheid and T. Welton, Wiley-VCH, ISBN 3-527-30515-7). In a possible embodiment of the chemical reactions according to the invention, the auxiliaries used are chemically substantially inert. In a preferred embodiment of the chemical reaction according to the invention, the auxiliary according to the invention can perform a further function in the chemical reaction, for example as a starting material, intermediate, product, (co)solvent, solubilizer and/or catalyst, preferably as a starting material, product, (co)solvent or solubilizer, particularly preferably as a starting material, (co)solvent or solubilizer.

The invention also relates to methods in which at least one sparingly volatile fluid, in particular ionic liquids and/or polymers, are used as stabilizers and which are characterized in that these are freed from volatile components in at least one associated process step by the purification method according to the invention.

Moreover, the invention also relates to methods in which sparingly volatile fluids, in particular ionic liquids and/or polymers, are used as lubricants and which are characterized in that these are freed from volatile components in at least one associated process step by the purification method according to the invention.

The invention also relates to products which are obtainable with the aid of the separation method according to the invention, the chemical reactions according to the invention and/or the method according to the invention.

The invention is explained in more detail below with reference to the following example, but without limiting it thereto.

BRIEF DESCRIPTION OF THE DRAWINGS

Table 1 shows the measured physical data in relation to the ionic liquid (IL) [bmim][$PF_6$].

Table 2 shows the parameters for the NRTL model in Aspen Plus®

Table 3 shows the calculated flows of the process described by way of example (from FIG. 2).

Equation 1 for calculations of activity coefficient according to the NRTL activity coefficient model of H. Renon and J. M. Prausnitz (AIChE Journal 14, 1968, page 135) in the form used in Aspen Plus®: Version 11.1.1.

EXAMPLE

A process as shown schematically in FIG. 2 is considered, in which the ionic liquid 1-n-butyl-3-methylimidazolium hexafluorophosphate [bmim][$PF_6$] is used as an entrainer in the extractive distillation in order to permit the separation of the azeotropic mixture of cyclohexane and benzene in a distillation column.

p-dichlorobenzene (p-DCB) is used as an auxiliary for the purposes of the invention in order, after the top product cyclohexane has been separated off in the extractive rectification column, to free the entrainer to be recycled from benzene in a second distillation column by means of rectification. The p-DCB is circulated together with the ionic liquid since small amounts of p-DCB in the extractive distillation do not present problems. Separation of the benzene as completely as desired in an industrially useable manner from the sparingly volatile [bmim][$PF_6$] is thus possible for the first time by distillation.

The following are chosen as process parameters in this example:

Mixture to be separated: 0.9 t/h of benzene+0.1 t/h of cyclohexane,

Separation auxiliary for column 1:1.5 t/h of [bmim][$PF_6$], 0.1 t/h of p-dichlorobenzene Column 1: 27 trays, feed: 14th tray, entrainer addition: 3rd tray, 800-815 mbar, reflux=0.25 t/h Column 2: 18 trays, feed: 11th tray, 150-160 mbar, reflux=0.45 t/h A simulation calculation carried out using the process simulator Aspen Plus® gives the mass flow rates in the process. The required properties of the ionic liquid, such as the density at various temperatures or the activity coefficient of components to be separated and of the auxiliary in the ionic liquid at infinite dilution, which were present neither in the Aspen Plus® database nor in the available literature, were determined by means of our own measurements and are listed in table 1. The densities were determined by means of a pyknometer and the activity coefficients by means of inverse gas chromatography (analogous to A. Heintz, D. Kulikov, S. Verevkin in J. Chem. Eng. Data 2001, 46, 1526-1529 and the sources stated there).

For simulation of the equilibria in Aspen Plus®, the NRTL activity coefficient model (see above) was used and the parameters are listed in table 2. For simplification, it is assumed that the density of the ionic liquid is linear with respect to the temperature and the activity coefficients at infinite dilution in the ionic liquid are independent of the temperature.

Table 3 shows the properties of the streams of this process: 99.74% of the cyclohexane used leave the top of the extractive distillation column (column 1) with a purity of 99.77% by weight. This stream contains only 0.2% by weight of benzene and 0.03% by weight of p-DCB as impurities. 99.98% of the benzene used are recovered at the top of purification column (column 2)—contaminated with only 0.03% by weight of cyclohexane. The ionic liquid leaves the purification column at the bottom together with the p-DCB and is recycled to the extractive distillation column. Owing to the low vapor pressure of p-DCB, 3 trays above the entrainer feed are sufficient to keep the p-DCB contamination in the cyclohexane at 0.03% by weight. The small losses of the auxiliary p-DCB, which arise because small amounts thereof enter the top product of column 1, are compensated by continuously feeding 0.03 kg/h of fresh p-DCB to the entrainer feed of column 1.

TABLE 1

| | Temperature in ° C. | | |
| --- | --- | --- | --- |
| | 20 | 110 | 169.6 |
| | IL density in kg/m³ | | |
| | 1376 | 1303 | 1253 |
| | Cyclohexane | Benzene | p-dichlorobenzene |
| Activity coefficient at infinite dilution in the IL at 100° C. | 17.9 | 1.87 | 4.35 |

TABLE 2

| | Comp. i | | | | | |
| --- | --- | --- | --- | --- | --- | --- |
| | Cyclohexane | p-DCB | Benzene | Cyclo-hexane | Cyclo-hexane | p-DCB |
| | | | Comp. j | | | |
| | Benzene | Benzene | IL | p-DCB | IL | IL |
| $a_{ij}$ | 0 | 0 | 40 | 0 | 4 | 40 |
| $a_{ji}$ | 0 | 0 | 0.57 | 0 | 1.6495 | 1.5504 |
| $b_{ij}$ | −43.3406 | 273.0688 | 0 | 0 | 0 | 0 |
| $b_{ji}$ | 182.7545 | −315.3037 | 0 | 0 | 0 | 0 |
| $\alpha_{ij}$ | 0.3 | 0.3 | 0.3 | 0.3 | 0.3 | 0.3 |

TABLE 3

|  | Column 1 Feed | Column 1 Entrainer | Column 1 Top product | Column 1 Bottom product | Column 2 Top product |
|---|---|---|---|---|---|
| Stream in FIG. 2 | A + B | E + H | A | B + E + H | B |
| Temperature in °C. | 71.7 | 47.5 | 73.3 | 85.3 | 28.4 |
| Pressure in bar | 0.82 | 1.2 | 0.8 | 0.815 | 0.15 |
| [bmim][PF$_6$] (E) in kg/h | 0 | 1500 | 0 | 1500 | 0 |
| p-DCB (H) in kg/h | 0 | 99.97 (*) | 0.03 | 99.94 | 0 |
| Cyclohexane (A) in kg/h | 100 | 0 | 99.74 | 0.26 | 0.26 |
| Benzene (B) in kg/h | 900 | 0.3 | 0.2 | 900.1 | 899.8 |

(*) incL 0.03 kg/h of fresh p-DCB.

$$\ln \gamma_i = \frac{\sum_j x_j \tau_{ji} G_{ji}}{\sum_k x_k G_{ki}} + \sum_j \frac{x_j G_{ij}}{\sum_k x_k G_{kj}} \left( \tau_{ij} - \frac{\sum_m x_m \tau_{mj} G_{mj}}{\sum_k x_k G_{kj}} \right) \quad \text{Equation 1}$$

where $G_{ij} = \exp(-\alpha_{ij} \tau_{ij})$ and $\tau_{ij} = a_{ij} + \frac{b_{ij}}{T}$, $$\alpha_{ij} = \alpha_{ji} \text{ and } \tau_{ii} = 0.$$

T is the temperature in Kelvin
$x_i$ is the mole fraction of component i
$\alpha_{ij}$, $a_{ij}$ and $b_{ij}$ are the adaptable model parameters
$\tau_{ij}$ and $G_{ij}$ are auxiliary parameters which are defined by the above formulae
$\gamma_i$ is the activity coefficient of the component i Insignificant deviations from the theoretical calculations are possible as a result of limitations in the practical implementation.

The invention claimed is:

1. A method for separating mixtures of substances using one or more ionic liquids and/or polymers as a selective additive, wherein the one or more ionic liquids and/or polymers are freed from one or more volatile components by multistage rectification in a distillation unit, wherein
   (i) at least one volatile auxiliary is used;
   (ii) the at least one volatile auxiliary used in the bottom of the distillation unit contributes a significant proportion of at least 50% to the pressure owing to its partial pressure;
   (iii) the pressure in the bottom of the distillation unit minus the partial pressure of the at least one volatile auxiliary which prevails there does not exceed 10 mbar;
   (iv) the at least one volatile auxiliary used leaves the distillation unit for the most part together with the ionic liquids and/or polymers at the bottom;
   (v) the at least one volatile auxiliary has a partition coefficient which is higher than that of the ionic liquids and/or polymers but lower than the partition coefficient of the one or more volatile components; and
   (vi) the auxiliary is reused together with the one or more ionic liquids and/or polymers and is substantially circulated without removing the auxiliary.

* * * * *